(12) United States Patent
Fletcher et al.

(10) Patent No.: US 8,743,194 B2
(45) Date of Patent: Jun. 3, 2014

(54) HIGH NUMERICAL APERTURE TELEMICROSCOPY APPARATUS

(75) Inventors: Daniel Fletcher, Berkeley, CA (US); Wendy Hansen, Seattle, WA (US); Neil Switz, Oakland, CA (US); David Breslauer, Oakland, CA (US); Erik Douglas, Oakland, CA (US); Robi Maamari, Clayton, CA (US); Wilbur Lam, Albany, CA (US); Jesse Dill, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 660 days.

(21) Appl. No.: 12/826,375

(22) Filed: Jun. 29, 2010

(65) Prior Publication Data

US 2011/0009163 A1 Jan. 13, 2011

Related U.S. Application Data

(63) Continuation of application No. PCT/US2008/088646, filed on Dec. 31, 2008.

(60) Provisional application No. 61/018,537, filed on Jan. 2, 2008.

(51) Int. Cl.
*H04N 7/18* (2006.01)

(52) U.S. Cl.
USPC ............................................. 348/79; 348/61

(58) Field of Classification Search
USPC ................... 348/61, 79; 359/656; 422/82.05; 600/573; 455/418; 396/429
See application file for complete search history.

(56) References Cited

U.S. PATENT DOCUMENTS

| | | | | |
|---|---|---|---|---|
| 5,982,559 A | * | 11/1999 | Furutake | 359/656 |
| 6,606,413 B1 | | 8/2003 | Zeinch | |
| 6,950,241 B1 | | 9/2005 | Liang | |
| 2003/0078517 A1 | * | 4/2003 | Kensey | 600/573 |
| 2003/0103262 A1 | | 6/2003 | Descour et al. | |
| 2005/0001144 A1 | | 1/2005 | Cartlidge et al. | |
| 2005/0266839 A1 | * | 12/2005 | Paul et al. | 455/418 |
| 2006/0222567 A1 | | 10/2006 | Kloepfer | |
| 2007/0183930 A1 | * | 8/2007 | Roman | 422/82.05 |
| 2007/0280677 A1 | * | 12/2007 | Drake et al. | 396/429 |

FOREIGN PATENT DOCUMENTS

| | | |
|---|---|---|
| CN | 2722826 Y | 9/2005 |
| KR | 10-2005-0006623 A | 1/2005 |
| KR | 10-2005-0093291 A | 9/2005 |
| KR | 10-2005-0100745 A | 10/2005 |

(Continued)

OTHER PUBLICATIONS

Frean, J.—"Microscopic images transmitted by mobile cameraphone"—Trans. of the Royal Society of Tropical Medicine and Hygiene, vol. 101, Jul. 30, 2007, pp. 1053.

(Continued)

*Primary Examiner* — Allen Wong
(74) *Attorney, Agent, or Firm* — John P. O'Banion

(57) ABSTRACT

An imaging system consisting of a cell-phone with camera as the detection part of an optical train which includes other components. Optionally, an illumination system to create controlled contrast in the sample. Uses include but are not limited to disease diagnosis, symptom analysis, and post-procedure monitoring, and other applications to humans, animals, and plants.

6 Claims, 6 Drawing Sheets

(56) References Cited

FOREIGN PATENT DOCUMENTS

| WO | 2005/016135 A1 | 2/2005 | | |
|---|---|---|---|---|
| WO | 2006/083081 A1 | 8/2006 | | |
| WO | 2006-083081 A1 | 8/2006 | | |
| WO | WO 2006/083081 A1 * | 8/2006 | ............... | H04B 1/38 |
| WO | 2009088930 A2 | 7/2009 | | |

OTHER PUBLICATIONS

State Intellectual Property Office of P.R.C., First Office Action issued on Jul. 25, 2011, Patent Application No. 200880123463.X, translation (pp. 1-7), claims (pp. 8-12), original Chinese language version (pp. 13-15).

Rodriguez, W.R. et al.—"A Microchip CD4 Counting Method for HIV Monitoring in Resource-Poor Settings"—PLoS Medicine, vol. 2, issue 7, Jul. 2005, pp. 0663-0672.

Makinen, J. et al.—"Add-on laser reading device for a camera phone"—Optical Design and Engineering II, Proc. of SPIE vol. 5962, 2005, pp. 596228-1-596228-11.

Blaivas, M. et al.—"Ultrasound image transmission via camera phones for overreading"—Amer. Journ. of Emergency Medicine—vol. 23, 2005, p. 433-438.

Frean, J.—"Microscopic images transmitted by mobile cameraphone"—Trans. of the Royal Society of Tropical Medicine and Hygiene, vol. 101, 2007, pp. 1053.

Razdan, S. et al.—"The Camera Phone: A Novel Aid in Urologic Practice"—Urology, vol. 67, issue 4, Apr. 2006, pp. 665-669.

Dziadzio, M. et al.—"A still image of a transient rash captured by a mobile phone"—Clinical Rheumatology, vol. 26, 2007, pp. 979-980.

Korean Intellectual Property Office, International Search Report and Written Opinion issued Aug. 19, 2009, counterpart PCT International Application No. PCT/US08/88646, including claims examined, 10 pages.

Korean Intellectual Property Office (KIPO), International Search Report and Written Opinion issued on May 15, 2012, including claims searched, related PCT International Patent Application No. PCT/US2011/058466, pp. 1-16.

European Patent Office, Extended Supplemental Search Report (ESSR) issued on Jan. 2, 2014 for corresponding European Patent Application No. EP 08 87 0007 (pp. 1-7) with claims searched (pp. 8-13) pp. 1-13.

* cited by examiner

HIGH NUMERICAL APERTURE TELEMICROSCOPY APPARATUS

CROSS-REFERENCE TO RELATED APPLICATIONS

This application claims priority from, and is a 35 U.S.C. §111(a) continuation of, PCT international application number PCT/US2008/088646 filed on Dec. 31, 2008, incorporated herein by reference in its entirety, which claims priority from U.S. provisional application Ser. No. 61/018,537 filed on Jan. 2, 2008, incorporated herein by reference in its entirety.

This application is also related to PCT International Publication No. WO WO 2009/088930 published on Jul. 16, 2009, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to telemicroscopy, and more particularly to performing telemicroscopy using a wireless communication device that has an integrated camera, such as a cellphone or pda.

2. Description of Related Art

Telemedicine is a growing technology and is gaining acceptance in many medical fields, such as rheumatology and urology for diagnoses not requiring microscopy. For medical applications requiring high resolution microscopy, such as pathogen detection, state of the art microscopic images are typically transferred to a computer and transmitted via the Internet for "telemicroscopy" or "remote microscopy" applications. The only device coupled directly to a cellular phone provides low numerical aperture optics and inadequate magnification and resolution for most microscopy applications. Additional information concerning related art can be found in the following publications, each of which is incorporated herein by reference in its entirety:

Dziadzio M, Hamdulay S, Reddy V, Boyce S, Keat A, Andrews J. "A still image of a transient rash captured by a mobile phone." Clin Rheumatol. 2006 Apr. 4.

Razdan S, Johannes J, Kuo R L, Bagley D H. "The camera phone: a novel aid in urologic practice." Urology. 2006 April; 67(4):665-9.

Jukka-Tapani, M; K. Niemelae, H. Vasama, R. Mattila, M. Aikio, S. Aikio, J. Aikio. "Add-on laser reading device for a camera phone." Proc. SPIE. Vol. SPIE-5962, pp. 685695.2005.

Rodriguez W R, Christodoulides N, Floriano P N, Graham S, Mohanty S, et al. (2005). "A Microchip CD4 Counting Method for HIV Monitoring in Resource-Poor Settings." PLoS Med 2(7): e182.

Microscopy has a central place in medical diagnosis among other applications (plant pathology, epidemic tracking, materials science and evaluation, etc.). In the developed world, medical samples are prepared as slides, often (but not always) stained with a contrast agent (e.g. absorbing and/or fluorescent dye(s)), and placed on the stage of a large (~0.5-1 m tall, 50+ kg) research microscope fitted with a ~75 W halogen lamp and/or a ~75+ W arc lamp illumination source. Optics allow imaging by eye at magnifications of up to ~2000×, image capture with cameras (e.g. CCD cameras), and the use of a variety of contrast mechanisms well known to those of ordinary skill in the art, e.g. bright-field, fluorescence, dark field, oblique illumination, Hoffman modulation contrast, differential interference contrast (DIC), phase contrast, polarization microscopy, and the like. Captured images can be stored with patient records, emailed for purposes of medical consultation, and digitally processed if appropriate.

Much of this capability is unavailable in the developing world, for reasons including: cost; maintenance difficulty for delicate instruments; lack of supply chain for frequent replacement parts (arc lamps have lifetimes of only ~200 hrs); lack of electricity to power lamps, etc.; lack of associated computer and/or internet resources; lack of portability to remote villages; etc. Even in the developed world, expense, complexity, and portability issues prevent widespread use of microscopy for medical purposes in non-hospital settings such as at-home monitoring of patient blood counts during chemotherapy. As a result, sick, immunocompromised patients must risk infection to travel to central medical facilities for testing.

Microscopy is a vital and ubiquitous healthcare tool in modern hospitals and clinics. However, developing countries often lack access to both clinical-quality microscopes to gather patient data and qualified medical personnel to provide diagnoses and treatment. Even in the U.S. and other developed countries, it is difficult to use microscopy for medical purposes in a non-hospital setting such as in the home.

Camera-equipped cell phones ("camera phones") have optical systems that, due to the requirement of imaging large objects and fields of view (e.g. faces, people, or landscapes) onto small (~5 mm on a side) sensors arrays (e.g. CCD or CMOS imaging array sensors), using a small (~5 mm diameter, ~5 mm focal length lens systems) must: have low object-side numerical aperture (NA), typically ≤0.01; non-telecentric design, with limitations known to those with ordinary skill in the art and including non-uniform collection efficiency across the field of view, and changes in the apparent magnification of an image with defocus; optical magnifications (M) (defined as from the object to the image on the sensor array) of <1, typically <0.03. For example, in the work by Jukka-Tapani Makinsen et al. (cited above) the optical magnification was ≤2.3, typically ≤1.5, indicating the unusualness of the present invention (all magnification beyond that in their system being done in software, not optically, and hence not increasing optical resolution). Furthermore, they have no associated trans-illumination system (e.g. as required for phase-contrast microscopy). Thus, there is not presently available a telemicroscopy apparatus based on a cell phone or similar device designed to be used for telemedicine applications.

BRIEF SUMMARY OF THE INVENTION

Accordingly, an aspect of the invention is to couple high numerical aperture optics to a cellular camera phone or other telecommunications device. Such an optical system would allow high-resolution microscopy and immediate transfer of data via existing telecommunications networks and would be useful for-but not limited to-disease diagnosis. By way of example, and not of limitation, the invention pertains to a microscopy device coupled directly to a cellular telecommunications and image acquisition device (such as a camera phone) with immediate data transmission capability. Importantly, this "telemicroscopy" device would include high numerical aperture optics allowing acquisition of high resolution images necessary for most microscopy applications.

In one embodiment, a readily-available hand-held communications device having imaging capabilities is modified or improved to include at least a second imaging lens that allows a collection NA of >X, wherein X may most generally be a range of values greater than 0.001, and more preferably greater than 0.1.

In various embodiments, the hand-held device may be a cell phone, pda or other device that has an integrated imaging system (e.g., built-in camera) and wireless communication capability. It will be appreciated that devices of this type typically image with a collection NA<0.001.

Accordingly, another aspect of the invention is an optical system which can be attached to, or integrated with, a hand-held communications device that has a camera.

Another aspect of the invention is the use of a telecentric collection lens system in combination with a camera in a hand-held communications device.

Still another aspect of the invention is to provide for dark-field, phase, fluorescence, epi-illumination, or other microscopy techniques in conjunction with a camera in a hand-held communications device.

In various modes of operation, the invention provides for biological imaging capabilities. In one embodiment, the invention includes an illumination system. It should be noted that for a thin and/or translucent sample (e.g. blood), transmission-based illumination would be appropriate (the light source being behind the sample.) For other samples that are not translucent (e.g. a wound) reflected light must be collected by the optical system (the light source shines onto the sample and is at least partly reflected therefrom.) This is well understood by those familiar with microscopy; however, it is an important addition to the present invention, considering that the inventive microscopy system could be used for either sample type.

Another aspect of the invention is to provide a variable range of magnification for imaging various samples. In one embodiment, the invention has a range of magnification of approximately 5× to 20× for imaging samples such as skin or wounds. In another embodiment, the invention has a range of magnification of approximately 20× to 50× for imagining smaller samples such as blood cells. In a further embodiment, the invention has a range of magnification of 5× to 50× for imaging samples of various sizes.

An aspect of the invention is a telemicroscopy apparatus, including a portable, hand-held cellular or other wireless communications device, said communications device having an image capture device therein; and a microscope lens system associated with said image capture device; wherein said microscope lens system has a collection numerical aperture (NA) of at least approximately 0.1 and a magnification (M) of at least about 1.

Another aspect of the invention is a telemicroscopy imaging system, including a portable, hand-held housing; an image sensor mounted in the housing; collection optics mounted in the housing and aligned with the image sensor, the collection optics having a collection numerical aperture (NA) of at least approximately 0.1 and a magnification (M) of at least about 1; a sample holder mounted in the housing and aligned with the collection optics; an illumination source mounted in the housing and positioned to illuminate the sample holder; a wireless transmission unit mounted in the housing for transmitting data from the image sensor; and a microprocessor mounted in the housing for controlling data collection, analysis and transmission.

A further aspect of the invention is a telemicroscopy method, including imaging a sample at a first location using a telemicroscopy apparatus, including a portable, hand-held cellular or other wireless communications device, said communications device having an image capture device; and a microscope lens system associated with said image capture device; wherein said microscope lens system has a collection numerical aperture (NA) of at least approximately 0.1 and a magnification (M) of at least about 1; and transmitting sample images and information derived therefrom from the communications device to a second location.

The invention further includes the following aspects:

1. An imaging system, comprising: a wireless communications device, said wireless communications device having an image capture device and a device lens; and an auxiliary lens associated with said image capture device and said device lens; wherein said auxiliary lens in combination with said device lens has a collection numerical aperture (NA) of at least approximately 0.001.

2. A system as recited in aspect 1: wherein said auxiliary lens has an object side and an image side; wherein said auxiliary lens is telecentric on said object side, or said image side, or both said object side and said image side.

3. A system as recited in aspect 1, wherein said system is configured to collect fluorescence as part of a biological fluorescence assay.

4. A system as recited in aspect 1, wherein said system is configured to use dark-field illumination or any variation on a dark-field optical technique.

5. A system as recited in aspect 1, wherein said system is configured to use the phase-contrast technique.

6. A system as recited in aspect 1, wherein said system is configured to use modulation contrast techniques.

7. A system as recited in aspect 6, wherein modulation contrast comprises Hoffman modulation contrast.

8. A system as recited in aspect 1, wherein said system is configured to use the differential interference contrast technique (DIC).

9. A system as recited in aspect 1, wherein transmitted light microscopy is used to image a sample.

10. A system as recited in aspect 1, wherein said system is configured to use reflected light microscopy to image a sample.

11. A system as recited in aspect 1, wherein said system is configured to use light emitting diodes (LEDs) as an illumination source.

12. A system as recited in aspect 1, wherein said system is configured to use a monochromatic LED as an illumination source.

13. A system as recited in aspect 12, wherein said illumination source is configured to minimize the effect of chromatic aberrations.

14. A system as recited in aspect 12, wherein said illumination source is configured as a fluorescent excitation source.

15. A system as recited in aspect 1, further comprising a light source of one of more LEDs (or other illuminating sources) arranged to illuminate a sample.

16. A system as recited in aspect 1, further comprising one or more illumination sources (e.g. LEDs) angled at a sample plane to using reflected light microscopy.

17. A system as recited in aspect 1, further comprising a grid of one or more illumination sources configured to illuminate a sample using transmitted light microscopy.

18. A system as recited in aspect 1, wherein said system is configured to use Kohler illumination to evenly illuminate a sample.

19. A system as recited in aspect 1, further comprising a diffuser element to evenly illuminate a sample.

20. A system as recited in aspect 1, further comprising an illumination source powered by said wireless communications device.

21. A system as recited in aspect 1, wherein said system is configured for disease diagnosis, or for medical evaluation of a patient's symptoms or a biological assay such as hematological analysis, blood counts, immunoassays, examinations or recording of tissue sample morphologies or pathology, or for diagnosis or evaluation of malaria, yaws, rashes, or wounds, or for use in conjunction with a microfluidic device for disease or pathogen diagnosis, or as part of health monitoring in food service environments such as for inspection of surfaces for bacteria.

22. A system as recited in aspect 1, wherein said system is a part of the detection arm of a fluorescence assay, wherein the function of the emission filter for said assay is provided by the Color Filter Array (CFA) of the image capture device, or wherein the system is a part of the detection arm of a fluorescence assay where the separate color channels of the image capture device are used separately to conduct 2 or more parallel assays at different emission wavelengths, or wherein said system is a part of the detection arm of a fluorescence assay and the illumination is epi-illumination.

23. A system as recited in aspect 1: wherein said imaging capture device and said device lens include an autofocus mechanism that forms an focusing mechanism for said system.

24. A system as recited in aspect 1, wherein said system is configured for optical detection in a biological assay and the pixels are binned to reduce image noise.

25. A system as recited in aspect 1, wherein said system is configured for materials analysis inspection of a metal part for metal fatigue, or evaluation of a weld, or evaluation of a component (e.g. a contact) in a micro-circuit.

26. A system as recited in aspect 1, wherein said system is configured for imaging a sample stained with any of the standard biological tissue stains.

27. A system as recited in aspect 1: wherein said system is configured for collecting autofluorescence of biological samples under ultraviolet excitation; and wherein said excitation can be of any wavelength between 200 and 400 nm, or a combination thereof.

28. A system as recited in aspect 1, wherein said system is a part of the detection arm for quantification or comparison of protein concentration in a solution(s), or is a part of the detection arm for quantification or comparison of protein concentration in a solution(s) wherein the wavelength used for protein concentration evaluation is converted to a visible wavelength (or to one which transmits the device lens and color filters) by a phosphor element or screen, or is the detection element in a multichannel-plate intensifier in a system.

29. A system as recited in aspect 1, wherein said system is part of the detection arm of a system for performing a DNA-based assay, or for performing a bioassay wherein illumination is supplied by a laser diode, or for performing a bioassay wherein illumination is supplied by an ultraviolet LED, or for performing a bioassay wherein illumination is supplied by a LED.

30. A system as recited in aspect 29, wherein the LED produces a power of >1 mW or wherein the LED produces a power of >5 mW.

31. A system as recited in aspect 1, further comprising an aperture stop which is not co-local with the device lens.

32. A system as recited in aspect 1, wherein the auxiliary lens has an aperture smaller than the clear aperture of the device lens.

33. A system as recited in aspect 1, wherein said lenses are immersion lenses, to achieve higher magnification.

34. A system as recited in aspect 1, wherein said auxiliary lens is removable.

35. A system as recited in any of aspects 1-34, wherein the auxiliary lens in conjunction with the device lens, provides a symmetrical 1:1 imaging system.

36. A system as recited in any of aspect 1-34, wherein said system is used for evaluation of humans, animals, or plants (for crop health and disease evaluation).

37. A system as recited in any of aspect 1-34, wherein the optical system includes an apodizing filter to compensate for "$\cos^{4th}$"-type vignetting effects for off-axis image points.

38. A system as recited in any of aspect 1-34, wherein the total system magnification M is M≥0.01, or M≥0.1, or M≥0.2, or M≥0.5, or M≥0.9, or M≥1.0.

39. A system as recited in any of aspect 1-34, wherein the auxiliary lens is a zoom lens.

40. A system as recited in any of aspect 1-34, wherein the collection NA is selected from the group consisting of NA≥0.01, NA≥0.1, NA≥0.2, NA≥0.3, NA≥0.4, NA≥0.5, NA≥0.6, NA≥0.7, NA≥0.8, and NA≥0.9.

41. A system as recited in any of aspect 1-34, wherein said auxiliary lens provides for object magnification.

42. A system as recited in aspect 41, wherein said magnification is selected from the group consisting of ≥5×, ≥10×, ≥15×, ≥20×, ≥25×, ≥30×, ≥35×, ≥40×, ≥45×, and a ≥50×.

43. A system as recited in aspect 42, wherein said magnification is variable.

44. A system as recited in aspect 1, further comprising a program running on said wireless device which sends a signal to an external device which is part of the system or its mechanical components based on analysis of an image taken by the device camera.

45. An apparatus for use in combination with a wireless communications device, said wireless communications device having an image capture device and a device lens, the apparatus comprising: an auxiliary lens associated with said image capture device and said device lens; wherein said auxiliary lens in combination with said device lens has a collection numerical aperture (NA) of at least approximately 0.001.

46. An apparatus as recited in aspect 45 in combination with any of aspects 2-44.

47. An apparatus according to any of the aspects, embodiments, modes or features described herein Further aspects of the invention will be brought out in the following portions of the specification, wherein the detailed description is for the purpose of fully disclosing preferred embodiments of the invention without placing limitations thereon.

BRIEF DESCRIPTION OF THE FIGURES

The invention will be more fully understood by reference to the following figures which are for illustrative purposes only.

DETAILED DESCRIPTION OF THE INVENTION

The present invention is a device which combines many of the benefits of the medical instruments with portability, low power consumption, cellular data transfer capability, and lower cost. In the simplest implementation, additional optics are attached to a standard camera-phone (cell phone with built-in camera). Such a system can also have software that assists in image acquisition, image processing (e.g. counting of the bacilli in a tuberculosis-positive sputum smear), appending patient information to the image or data derived from the image, and uploading of the information to a server or other computer system (possibly including another phone) for diagnosis, medical consultation, general record keeping (e.g. for reimbursement purposes), epidemic tracking or general epidemiology, etc. Furthermore, information can be downloaded to the phone in use, e.g. to provide patient record data for patients to be seen the next day, synchronize records, provide updated results from other tests, scheduling reminders about which patients need follow-up tests, etc. The advent of GPS (global positioning system) capability on cell phones also allows for location-tagging all data, especially useful for tracking patients in rural areas of developing counties, and for location-based notifications, e.g. reminding a technician passing through an area to check on a local patient due for a follow-up test. Obviously there are other uses for a system with such capabilities, including tracking packages or general logistics, plant pathology, monitoring of bioterrorism or biowarfare, materials research or testing, e.g. of welds in bridges and the like, etc. Such a system could also include mechanisms for sterilizing the sample area after use, e.g. by irradiation via a built-in ultraviolet light emitting diode, or mechanisms to automate or partially automate sample preparation, e.g. microfluidics devices or other fluid handling systems to allow for automated staining of a sample in preparation for imaging, e.g. built-in fluid-handling, and/or built-in sample heaters or forced-air systems for fixing samples.

Figure 1:
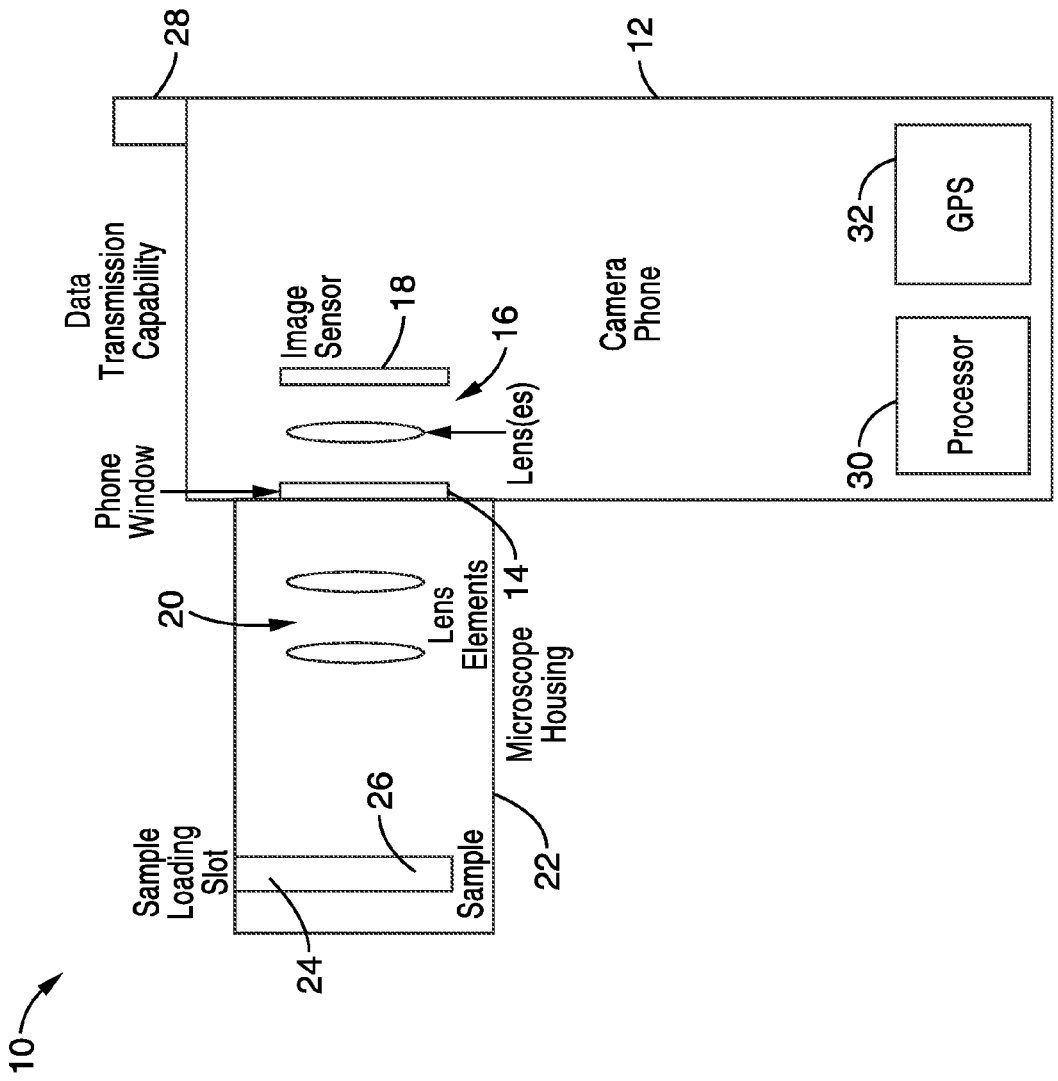
FIG. 1 is a schematic diagram of an embodiment of a telemicroscopy apparatus based on a cell phone according to the present invention

As shown in FIG. 1, a telemicroscopy apparatus 10 is formed from a camera phone 12. Camera phone 12 is a standard cellular phone with an imaging system made up of window 14, lens(es) 16, and image sensor 18 positioned to function as a camera, i.e. record images on image sensor 18, typically a CCD device. Camera phone 12 is made into a microscope by attaching a microscope lens system 20 mounted in a microscope housing 22 to camera phone 12. Microscope lens system 20 is made up of one or more lenses (e.g. two as shown) to provide suitable numerical aperture and magnification. Microscope housing 22 removably attaches to camera phone 12, e.g. snaps on or screws on, and positions microscope lens system 20 in alignment with image sensor 18. Housing 22 also includes a sample loading slot 24 in which a sample 26, e.g. a microscope slide or a microfluidic device containing a medical specimen, may be placed. Microscope lens system 22 allows a microscopic image of any sample 26 to be projected onto image sensor 18. An illumination source can also be provided.

The camera phone 12 and microscope housing 22 form a telemicroscope apparatus 10 by virtue of the data transmission capability of cell phone 12, as represented by antenna 28. Telemicroscope apparatus 10 can thus transmit microscope images of a sample 26 recorded by image sensor 18 wirelessly to a remote receiver. Camera phone 12 may also include a processor 30 that may be used to analyze the recorded images, and a GPS unit 32 that may be used to determine location and transmit location information with the images.

While a standard camera phone 12 may be used as is, device lens(es) 16 are generally designed to demagnify an image. Therefore, device lens(es) 16 may be removed from cell phone 12. In either case, microscope lens system 20 is designed so that either alone where device lens(es) 16 are removed, or in combination with the device lens(es) 16, a suitable numerical aperture (NA) and (object-to-image) magnification (M) for microscopy are obtained. Typically these values will be NA of at least approximately 0.1 and M of at least about 1, and more preferably NA of at least approximately 0.3 and M of at least about 4.

Figure 2:
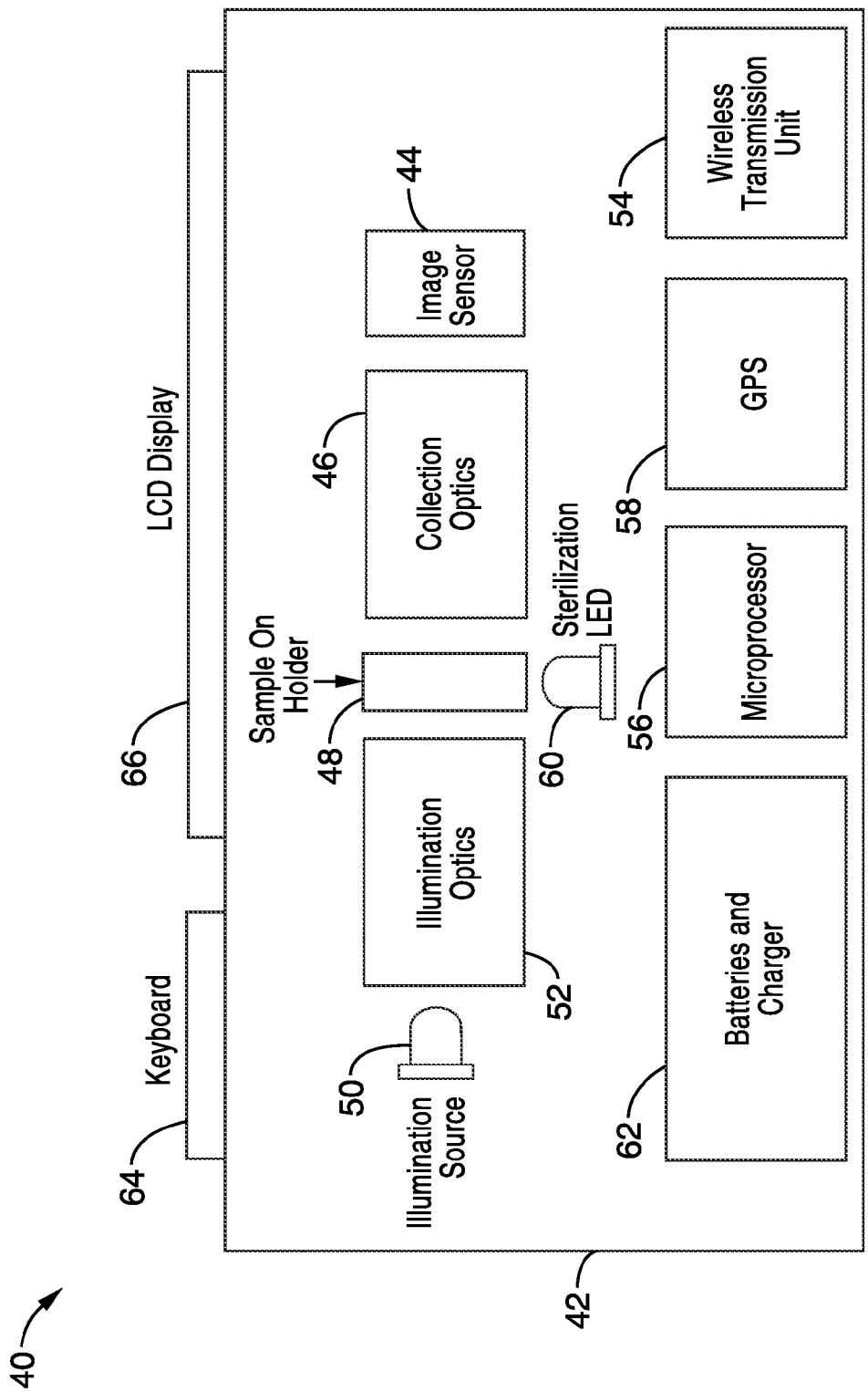
FIG. 2 is a schematic diagram of an alternate embodiment of a telemicroscopy apparatus according to the present invention

FIG. 2 shows a telemicroscopy apparatus 40 that is similar to that of FIG. 1 in its function but is built without a standard cell phone. Telemicroscopy apparatus 40 is formed of a portable hand-held housing 42, and has an image sensor 44, collection optics 46 and a sample holder 48 in which a sample may be placed. Image sensor 44, collection optics 46 and sample holder 48 are aligned so that images of the sample are recorded by sensor 44. Collection optics 46 are configured to function as a microscope, e.g. NA of at least approximately 0.1 and M of at least about 1, and more preferably NA of at least approximately 0.3 and M of at least about 4.

Apparatus 40 also includes an illumination system formed of an illumination source 50 and illumination optics 52 aligned to illuminate sample holder 48. Apparatus 40 also includes a wireless transmission unit 54 for transmitting recorded images, and may also include a microprocessor 56 and GPS unit 58. Apparatus 40 may also include a sterilization LED 60 positioned to apply sterilizing radiation, e.g. UV, after use. Apparatus 40 also includes batteries and charger 62, a keyboard 64, and an LCD display.

Figure 3:
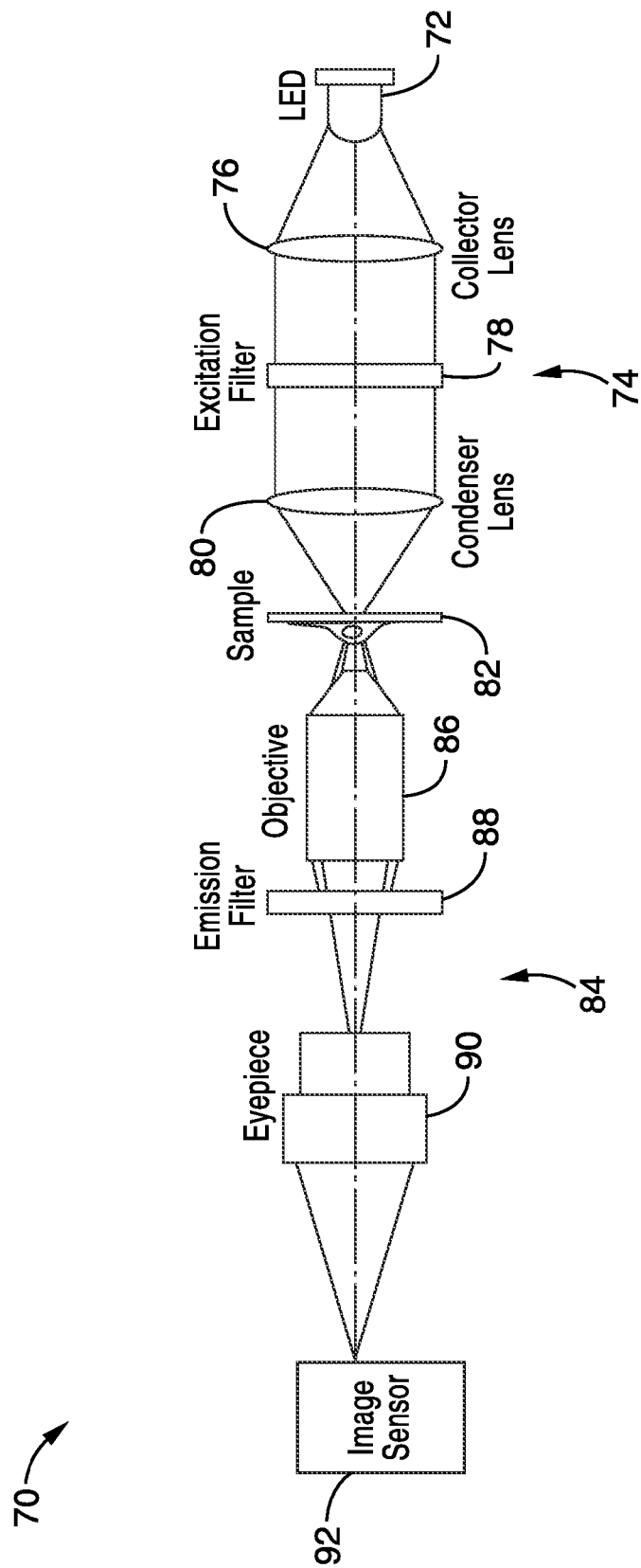
FIG. 3 is a schematic diagram of an optical system, having transmission-based illumination, according to the invention.

An illustrative optical system 70 that may be utilized in the apparatus 40 of FIG. 2 or apparatus 10 of FIG. 1 is shown in FIG. 3. Light from a source 72, e.g. LED, is transmitted through illumination optics 74, which include a collector lens 76, an excitation filter 78, and a condenser lens 80, onto a sample 82. Light from sample 80 passes through collection optics 84, which includes objective 86, emission filter 88, and eyepiece 90, to image sensor 92.

Figure 4:
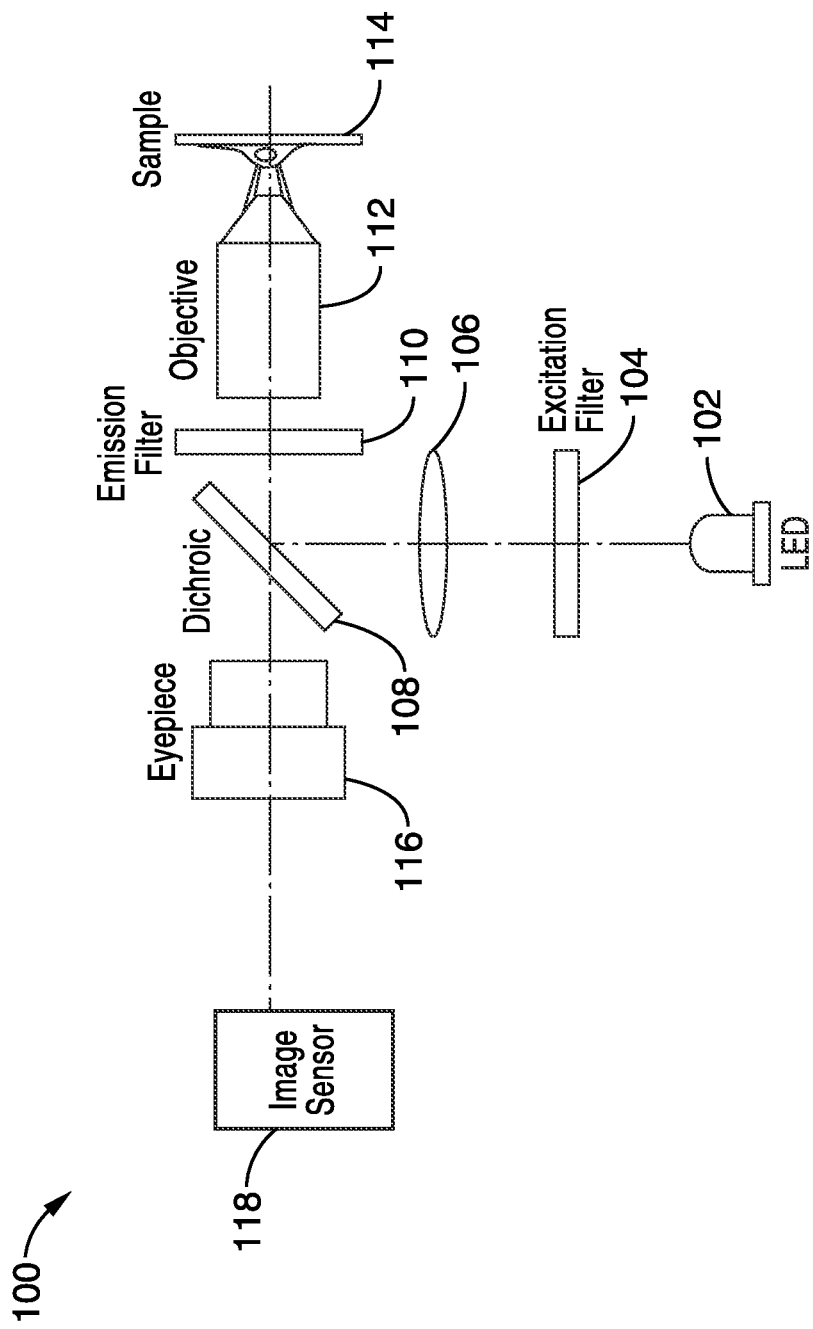
FIG. 4 is a schematic diagram of an alternate optical system, configured for epi-illumination, according to the invention.

An alternative optical system 100 configured for epi-illumination is shown in FIG. 4. Light from a source 102, e.g. LED, passes through excitation filter 104 and condenser lens 106 to a dichroic 108 which reflects the light though emission filter 110 and objective 112 to sample 114. Light, e.g. fluorescence, from sample 114 passes through objective 112, emission filter 110, dichroic 108, and eyepiece 116 to image sensor 118.

FIGS. 3-4 illustrate that various optical components can be used in different configurations to provide illumination and magnification. The optical components can further be configured to provide any of the contrast mechanisms used in microscopy to add this feature to the telemicroscopy systems of the invention.

Figure 5:
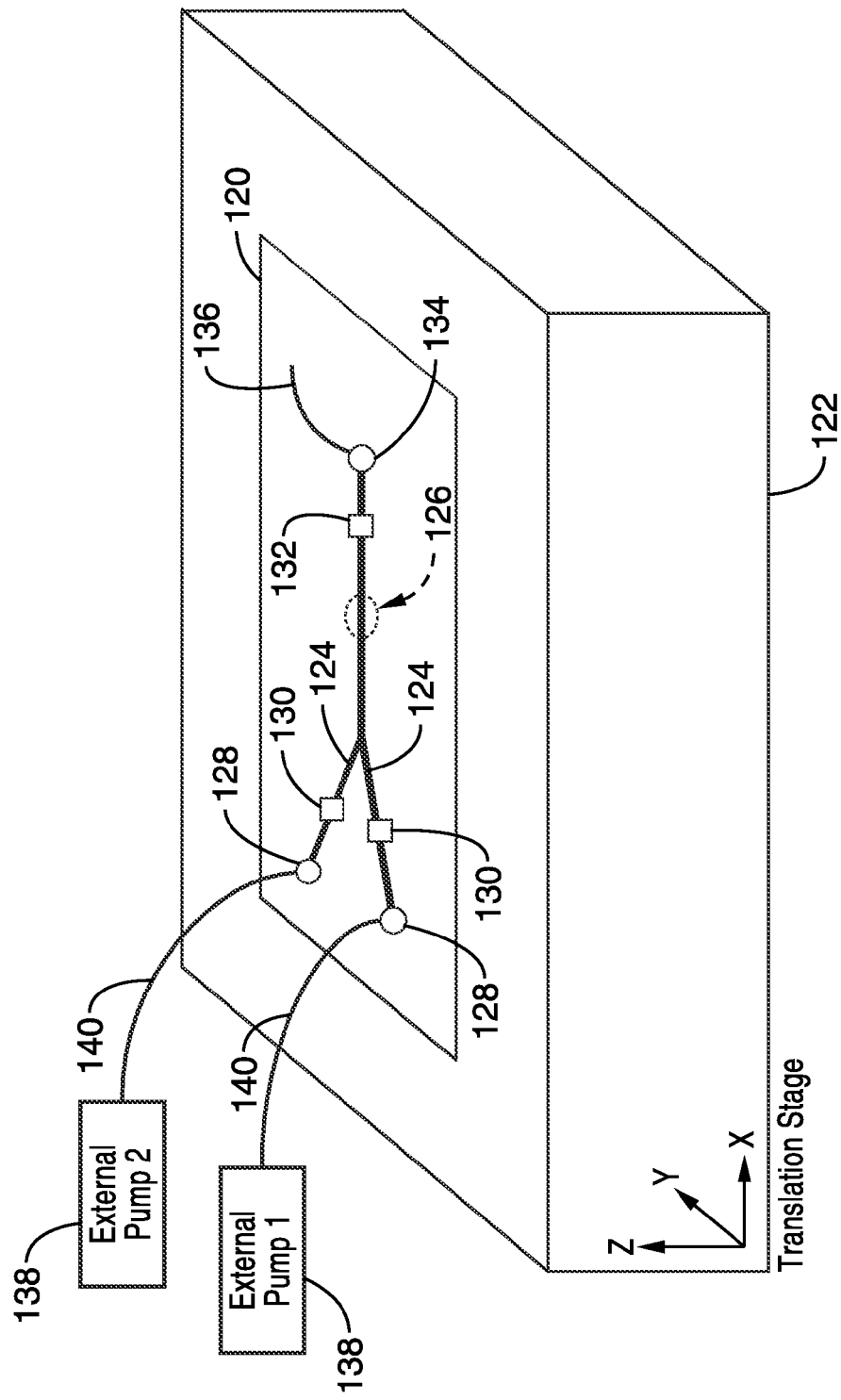
FIG. 5 is a schematic diagram of a microfluidic sample device according to the invention.

FIG. 5 illustrates a microfluidic sample device 120 on a translation stage 122. Translation stage 122 may be moved in the x-y-z directions to allow sample examination. Microfluidic sample device has one or more fluid channels 124 (e.g. two as shown) which come together into one channel at an interrogation area 126 at which the microscope system is aimed. Each channel 124 has a fluid input 128 at which a sample, e.g. a drop of blood, may be input, and an inlet valve 130 which controls access to the interrogation area 126. There is an outlet valve 132 after the interrogation area 126 and a fluid outlet 134, which may be connected to an outlet line 136. An external pump 138 may be connected to each fluid input 128 by an inlet line 140 and may be used to add fluid, e.g. stain, to the system or to flush out the system.

Figure 6:
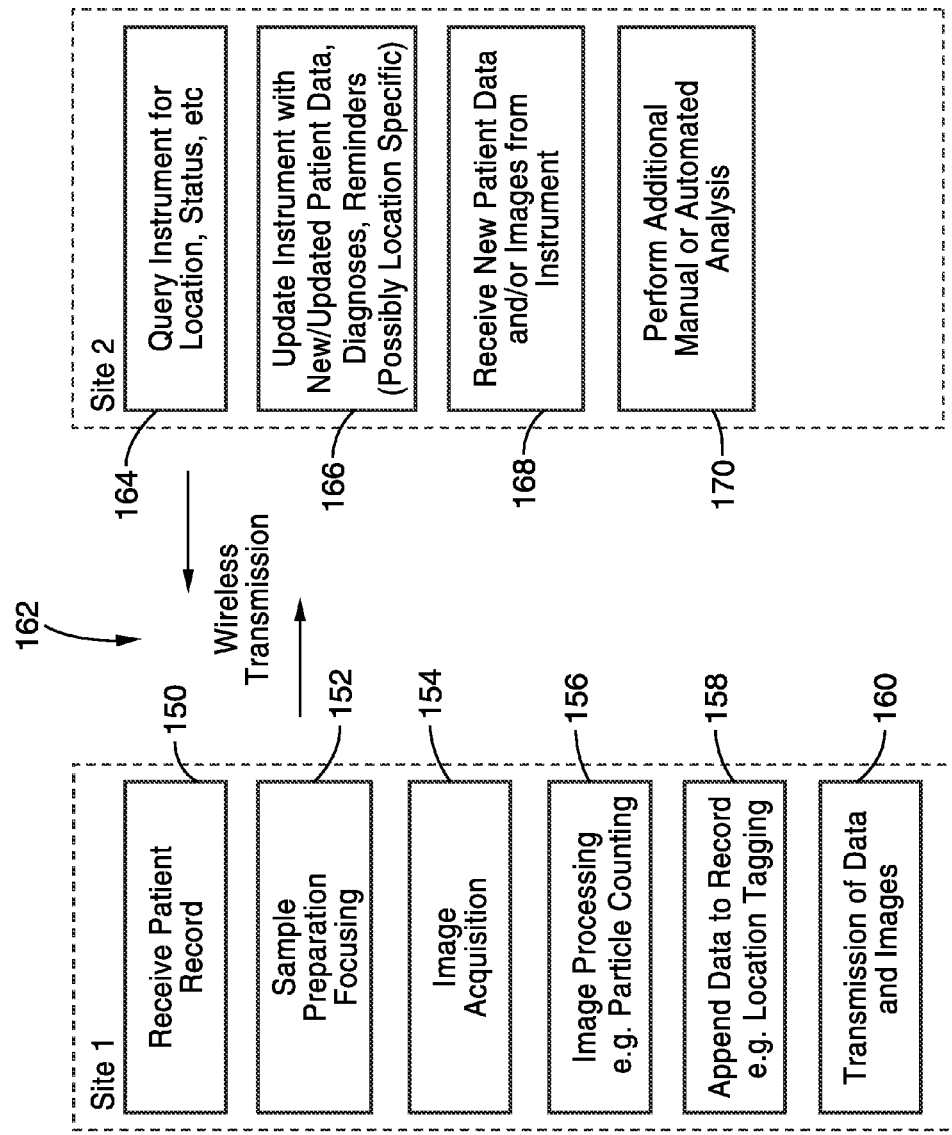
FIG. 6 is a flow chart of an embodiment of a method according to the invention.

FIG. 6 illustrates an application of the invention to telemedicine. At a first site, site 1, the telemicroscopy apparatus of the invention can be used to perform any of the following: receiving patient records (step 150); sample preparation, including focusing the microscope on the sample (step 152); image acquisition (step 154); image processing, e.g. particle counting (step 156); appending data to record, e.g. location tagging (step 158); and transmission of data and images (step 160). At a second site, site 2, the following can be performed: the telemicroscope at site 1 can be queried for location, status, etc. (step 164); the telemicroscope at site 1 can be updated with new or updated patient data, diagnoses, or reminders (possibly location specific) (step 166); new patient data and/or images can be received from site 1 (step 168); and additional manual or automated analysis can be performed (step 170). All transmission between site 1 and site 2 is by wireless transmission 162.

Some of the main features of the invention include:
1. NA>0.1, 0.2, etc.
2. Cellular or satellite (as opposed to just Wi-Fi) communication enabled.
3. GPS or location-sensing enabled.
4. Use for medical application, e.g. for certain disease diagnosis, or disease tracking.
5. With automated image evaluation for medical content, and/or remote diagnosis based on transfer of images or image information.
6. With use of standard microscopy contrast techniques—fluorescence, darkfield, phase-contrast, etc.

More specifically, important features and aspects of the invention include:
1. Portable, hand-held, low weight, small size.
2. Numerical aperture ≥X, where X is one of a range, preferably starting at 0.1 and more preferably at 0.3.
3. Optical magnification from sample to imaging sensor array (e.g. CCD). Typically this will be <<1 in standard camera phone, since most cameras are designed to capture large areas on a small sensor. The SPIE paper cited above has a maximum M~2.3. For our purposes, M>1, M>5, M>10, or M>20 and greater; in particular, the Nyquist criterion requires a minimum magnification to avoid aliasing in a digital image acquisition, given by:

$$M \geq (\text{pixel spacing}) * 2 * NA/\lambda \text{ (to avoid aliasing)}$$

For typical λ=0.5 μm, pixel spacing ~5 μm, and moderate NA~0.25, this amounts to M≥5. For NA=0.4, and a pixel spacing of 7.4 μm (as in a prototype camera), this becomes M≥11.8, etc. Such high magnifications are only useful if collecting images of small areas.

4. GPS/location sensing/reporting/record tagging.
  (a) Prompting to visit local patients due for tests.
  (b) Tagging of patient data with location.
5. Automatic image processing.
  (a) For full diagnosis.
  (b) Selective transmission (region of interest of an image).
  (c) Automated counting of items (e.g. bacilli) in an image.
  (d) Discrimination of items in an image for diagnosis or other purposes.
  (i) E.g. size (e.g. to distinguish different blood cell types).
  (e) All above for blood cells, bacilli, parasites.
6. Built in staining/labeling/dilution of a sample.
  (a) Using microfluidics.
  (b) Any fluidics.
7. Sterilizing LED (e.g. UV LED in sample area actuated to sterilize it between samples).
8. Contrast techniques.
  (a) Fluorescence.
  (b) Darkfield.
  (c) Phase contrast, oblique illumination, DIC, Hoffman modulation contrast, etc.
9. Tele- (wireless connectivity, notably beyond Wi-Fi).
  (a) To receive diagnosis, updates to patient records or schedules of who to visit.
  (b) To upload data for:
  (i) Record keeping.
  (ii) Tracking.
  (iii) Diagnosis.
  (c) Upload images for remote diagnosis (possibly automated).

Distinguishing features of the present invention include the use of high-numerical-aperture collection optics on a hand-portable system; coupling of the system preferentially to the cellular-phone network, or to wireless (e.g. 802.11-type systems), Bluetooth, radio, or other wireless systems; capability to wirelessly transmit data to other devices, especially a computer server for the medical records (e.g. at a hospital or doctor's office); optical magnification from the imaged object to the imaging sensor (e.g. CCD) sufficient to enable resolution at the limit allowed by the high-numerical-aperture collection optics; location-tagging of records and/or location-based notifications based on GPS or cellular-tower triangulation or the like; the use of contrast mechanisms typically used in microscopy with a handheld, wireless-data-transfer-capable device (e.g. bright-field, fluorescence, dark field, oblique illumination, Hoffman modulation contrast, differential interference contrast (DIC), phase contrast, polarization microscopy, and the like); and built-in sterilization or fluid handling systems.

There are many other advantageous and unusual aspects of the invention.

The invention may also include the device as described but transmitting data through means other than wireless telephone signals (Bluetooth, cable to laptop, infrared, etc).

The invention may also include the device as described but with some or all of the microscopy components (lenses, filters, apertures) integrated on-chip with the image sensor, rather than as part of a clip-on attachment. The integrated on-chip system could switch between conventional imaging and microscopic imaging by the movement or adjustment of lenses or other components on-chip rather than the external adjustment of lenses.

The present invention would, of necessity for imaging at high-resolution, have: high numerical aperture, typically >0.1; magnification >1, such that the image is spread over sufficient pixels of the image sensor to allow for digital sampling of the image by the pixels at or above the Nyquist criterion, for preservation of all resolution information; and preferably be telecentric on the object-side to provide advantages for microscopy as listed above and as known to those with skill in the art. In a preferred embodiment the system would have NA≥0.3, M≥4, be object-side telecentric, and have an associated trans- or epi-illumination system for sample illumination.

Other useful embodiments could include optical magnification such that digital sampling of the image by the sensor array pixels occurs at less than the Nyquist criterion but such that the MTF (modulation transfer function) of the image is ≤25% at the spatial Nyquist frequency associated with the sensor pixel spacing, such that aliasing is not particularly apparent to the human eye when the image is presented on a screen; alternately the magnification could be chosen such that this limit could be set at ≥7%, the rough limit of MTF contrast detectable by the human eye. Choosing such lower magnifications has advantages e.g. in terms of allowing for imaging a larger field of view in the object for a given sensor size, and increasing the amount of light from a given sample which will contact a given sensor pixel in a given time.

Regarding portability, several factors in combination serve to increase this beyond that of a standard microscope and to make the system hand-portable: use of light-emitting diodes for illumination (eliminating the need for bulb changes or large or high-voltage power supplies), use of low-power embedded computing systems to eliminate the need for a stand-alone associated computer system; use of low-power CCD or other focal-plane sensory arrays for image acquisition; removing optics not associated with a primary measurement approach (e.g., no system of turrets to change objectives, or eyepieces for direct visual as well as digital imaging). The low-power nature of the system also allows for low battery weights (e.g. using lithium-ion batteries) in a system designed to operate for long (~several hour) periods without connection to a power grid. In a preferred embodiment, the system weigh is ≤2 kg and the system volume is ≤8 liters; in an even more preferred embodiment, system weight is ≤1 kg and system volume is ≤3 liters. (System volume is here defined as that of a box of dimensions sufficient to enclose the entire system).

Unlike current cellular-phone system connected cameras that are not designed for microscopy, but rather for large-area imaging (barcodes, faces, or larger areas) at low (typically >0.1 mm) resolution, the present invention is designed to image small areas (typically smaller than the imaging sensor) at high (<10 μm) resolutions in a cell phone or cellular-phone network connected system (e.g. an embedded system including capacity to link to the cellular phone network via the GSM or CDMA standards, or via orbital-satellite-connected phone systems). Additionally or separately the system may have the capacity to use Wi-Fi (802.11-type) or other wireless communication to connect or transmit data to other systems.

Particular advantages of the invention include the following:

1. Resolution: unlike existing cell-phone connected devices, the prototype optical system has resolution <2 μm, and in general would have resolution roughly ≤10 μm, an order of magnitude better resolution than typical cellular-network connected devices.

2. Magnification: sufficient to realize the advantages of the enhanced optical resolution, and several order of magnitude larger than typical cellular-system connected optical devices.

3. Location sensing: use of GPS or cellular-triangulation to establish location and use this information to tag images of samples, data derived from such images, or patient records with location data for use in epidemiology, patient monitoring or tracking, subsequent notification/reminders to a field technician to check on certain patients, record keeping (e.g. for purposes of reimbursement or reporting to granting agencies such as the World Health Organization), etc. This feature is currently unknown on optical systems designed to portable operation with resolutions of ≤10 μm.

4. Automated image evaluation for diagnostic purposes: acquired images can be processed either at a central facility (or distributed computing network, e.g. similar to SETI@Home), or in a preferred embodiment processed in real-time on the processor embedded in the device to provide information of medical relevance, e.g. a count of the bacilli found in the image. Typically a technician must painstakingly count the bacilli in multiple (often >10) images from each of several sample (>30 images total) to get the relevant data; operator fatigue, lack of time, failure to comply with required protocols, etc. serve to reduce counting efficacy and diagnostic accuracy. Automated counting of bacilli hence provides a significant benefit to medical personnel in terms of time (and thus cost) of doing an assay and in terms of accuracy of the results. More complicated processing algorithms (e.g. adaptive ones designed to allow speciation of malaria parasites from an image) are also be considered, as well as discrimination (e.g. based on size) of different samples (e.g. (possibly stained) white and red blood cells or parasites). In addition, regions of interest of selected images may be automatically chosen and appended for record keeping and/or subsequent verification by a human technician.

5. Contrast: Many contrast mechanisms, most notably fluorescence, are not available in the developing world, and also have not been implemented on cellular or wirelessly connected imaging systems. Fluorescence labeling and detection is frequently substantially advantageous for diagnostic assays, providing better contrast, enhanced specificity, and lower background, all allowing for easier image assessment by medical personnel. Use of high-numerical aperture optics in conjunction with sample excitation using, e.g., high-power light emitting diodes, and coupled with an inexpensive (~typical cellphone camera type) imaging sensor allow sufficient sample excitation, optical collection efficiency, and electrical detection sensitivity (e.g. quantum efficiency) that (e.g.) fluorescent tuberculosis bacteria can be easily imaged and automatically counted on a hand-portable device with cost potentially competitive with other developing-world-appropriate medical equipment. Other contrast mechanisms (e.g. dark-field or oblique illumination, phase contrast, etc.) can be similarly implemented in a comparatively inexpensive and hand portable system operable without an electrical connection (i.e., battery operated). For example, oblique-illumination could allow for distinguishing of certain blood cell types based on the amount of light scattered from the cells, in a manner analogous to that used in a flow cytometer.

6. Combination with sample preparation: One can also consider the addition of automated sample preparation (e.g. fluidic handling, drying, or heating) systems to the device, retaining small size and portability (e.g. via use of microfluidic devices for the fluid handling) while further automating the diagnostic procedures and lowering the skill level and other equipment required by the operator to perform the test or assay. For example, in one embodiment a chemotherapy patient could prick their finger, squeeze a drop of blood into a microfluidic chip cartridge, and insert the cartridge into the handheld microscope device. The device would implement automatic staining, dilution, and (e.g.) addition of anticoagulant of/to the blood using the microfluidic device (which may include micro- or standard valves for sample flow control), image some number of fields of view of the sample, count and discriminate different blood cell types, upload the data to the patient's physician, and turn on an ultraviolet light emitting diode to sterilize the microfluidic device for safe disposal and sample area for subsequent use.

Optical Design and Implementation

A. Camera Traits: Cell-phone cameras are typically small, defined perhaps by having lenses <1 cm in diameter, and have small CCD (or CMOS or other) detector arrays, typically of linear dimensions <1 cm as well. Pixel sizes are typically <10 μm on a side.

The devices are designed to image at object distances of greater than approximately 30 cm; usually the aperture of the optical system is defined by the lenses or mounting hardware for the lenses, and is of the order of several mm in diameter.

1. Consequently, object-side NA in the optical train is of the order of NA~0.005=(3 mm/2)/(30 cm).

2. The system aperture being located at or near the lens(es), and being smaller than the detector array, field angles in image space for the system (i.e., the field angles onto the detector array) are typically >0. Hence the system will suffer from "$\cos^{4th}$" intensity falloff for off-axis image points (as those with skill in the art will know, the "$\cos^{4th}$ rule" is not an exact predictor of the actual falloff).

3. The cameras may or may not be designed for best focus for infinitely distant objects. It is likely that the minimum image-plane spot sizes are obtained for object distances of several feet (one meter) or so. This will probably vary among different phone makes.

4. The detector arrays are typically CCD or CMOS chips with various pixel counts, usually 640×480 or greater. Pixel sizes are typically 3-10 μm on a side, and may or may not be square. Total array size is roughly the pixel-count times the pixel dimension along that axis, with possible additional factors due to details of the detector array architecture (e.g. non-100% fill-factor due to interline architecture, etc). The arrays are typically color, with an accompanying color filter array (CFA), e.g. a Bayer array, limiting the wavelengths of light incident on various pixels such that a color image may be obtained after proper interpolation. The detector arrays typically allow for "electronic shuttering" (e.g. via use of an interline-architecture CCD array); consequently the cameras typically do not have built-in mechanical shutters.

5. The user typically does not have access to gain, black level, shutter speed or other camera adjustments, though one can imagine this may change in the future.

6. It is possible to write software for the phones, which could in principle drive the camera. It is even possible to envision programs which automatically adjust the shutter speed or other camera parameters accessible within the operating system of the phone. Similarly, such a program could conceivably adjust or signal for adjustments to illumination, focus, or other external factors via electronic outputs from the phone (e.g. via the hands-free jack).

7. It would also be possible to add software for automatic image rejection based on poor quality, and software to stitch together multiple images (or aid in stitching together those images)

8. In terms of remote transmission of images, it would be possible to add the following additional software:
  (a) Image encryption.
  (b) Annotation of images with text or drawings.
  (c) Attaching data to images (e.g. patient information, diagnosis, geographic information, etc).
  (d) Automated image processing for disease diagnosis.

B. Design Features: Camera phones and the like are designed primarily for imaging larger objects, e.g. faces, people, buildings, etc. The present invention involves using such a device for imaging of smaller objects, particularly (but not limited to) objects smaller than the size of the detector array in the camera.

1. The optical invariant (aka Etendue) guarantees that $A_{image}/A_{object}=\Omega_{object}/\Omega_{image}$, where A=area of the object in the respective optical plane and $\Omega$=the solid angle into which light is radiating or propagating at that same optical plane. Note that the lateral magnification $M=\sqrt{(A_{image}/A_{object})}$. Furthermore, in the paraxial approximation $\Omega \propto NA^2$. Consequently, in the paraxial approximation $M\sim NA_{object}/NA_{image}$. In the discussion that follows this approximation will be used without being limited to the paraxial case, with the knowledge that for NAs outside the paraxial limit the equation involving $\Omega$ would need to be used instead for exact results.

2. One cannot achieve an NA~1 in air, nor above the index of the immersion medium if using immersion lenses. Without being limited to air as an immersion medium, that case will be discussed. Air has an index of ~1, so the maximum magnification achievable onto a cell-phone camera detector array is thus $M\sim 1/NA_{image}$. Assuming an NA (designed into the cell-phone camera) of $NA_{image}\sim 0.25$ (an NA in the range of 0.1-0.5 would be typical), this give the maximum M~4. For comparison, imaging a human face (~20 cm dia.) onto an ~5 mm CCD would require a magnification of M~0.025 in order to accommodate the entire face within the field of view. This being what the phones are designed for, their collection NA's are such as to provide magnifications of this order (or less).

3. At a (typical) magnification of M≤0.025, and assuming a detector pixel size of ~5 μm, the minimum resolvable feature in the object will be d=5 μm/0.025~200 μm, ignoring pixilation and aliasing questions.

4. Conversely, at a higher collection NA, the minimum resolvable feature would be d=5 μm/4~1.25 μm, again ignoring pixilation and aliasing questions.

5. The use of camera phones to image features which would ordinarily not be effectively resolvable with them; in order to do this, additional optics are required in order to boost the collection NA of the system.

C. Telecentricity: Telecentricity is defined by either the exit pupil or entrance pupil or both of an optical system being imaged at infinity. This has a number of important implications. As used herein, "telecentric space" will define the space on the image, object, or both side of the optical system in which the pupil is imaged at infinity. Important issues and advantages provided by telecentricity include:

1. equivalent Numerical Aperture (NA) for all points in the image or object plane which is in a telecentric space. As a result, e.g., if the object space is telecentric, then light collection efficiency is identical for all points in the object field—all points will appear equally bright, though this advantage can be lost if the system is not also telecentric on the image side (doubly telecentric system).

2. zero field angle, which leads to a lack of parallax issues when focusing into structures with depth (e.g. microwell plates). Hence wells at the edge of the field of view in a telecentric space will be imaged similarly to those on the optic axis.

3. Apparent magnification is independent of defocus. Consequently samples which are not properly focused, or are tilted (e.g. a mis-mounted or badly toleranced microscope slide) will not have distorted image sizes for the out-of-focus components, though obviously the resolution will degrade somewhat for those components.

4. If the image space is telecentric, then the point-spread-function for the optical system will be the same for all points in the image space. This can be a decided advantage in terms of imaging onto a CCD or interpreting images captured by a CCD (or CMOS or other) optical detector array.

5. Optical interference filters placed in the telecentric space will have transmission and/or reflection bandwidth independent of field position, due to the field angle and NA features mentioned above. Filters placed in the space in which the aperture stop resides (i.e. with no lenses between the filter and the aperture stop) will have the narrowest possible bandwidth, though it will vary with field position for different object or image points (or both)

These features are of significant advantage in microscopy, for which reason most microscope objectives are designed to be telecentric in the object space of the microscope. Often the microscope is also designed to be image-space telecentric (or roughly so) as well. Notably, it is very unlikely that the cell-phone camera is telecentric by design, both because of the nonuniformity of collection efficiency, but also because a telecentric system cannot image a field of view larger than the diameter of the final lens before the image (or object) plane that is in the telecentric space. Hence if the camera phone were to be object-space telecentric, it could have a field of view of only a few mm, the size of the entrance lens to the phone.

Hence telecentricity (and particularly object-space telecentricity) are is novel, since one would not normally consider so restricting the field of view, e.g., on the object side of the phone. However, in the case of additional lenses, this can be avoided by choosing lenses of the appropriate size for the field of view desired. With such a system, vital uniformity of magnification, collection efficiency, and lack of parallax, among other advantages, can be achieved, enabling the use of the system for sensitive microscopy and inspection tasks.

D. Numerical Aperture: Numerical aperture (NA) defines the resolution and light-gathering ability of an optical system. The term is well understood by those with ordinary skill in the art, and will not be explained here. However, in the paraxial approximation, the magnification of a system is inversely related to the ratio of NAs, as mentioned above. Since the camera-phone can image a ~2 m person onto a ~2 mm detector chip, and since the NA onto the detector chip is unlikely to be more than $NA_{image}$~0.5 due to reflection losses at high incident angle onto silicon or the like, the object-side NA must be $NA_{obj}$~0.5/100=0.005 or so. This is extremely low from the standpoint of microscopy or sensitive inspection, since the related resolution would be given by the Rayleigh criterion as $\delta$~1.22 $\lambda$/NA (~244$\lambda$ in this case, or ~0.1 mm assuming green light at $\lambda$~500 nm).

The coupling of additional lenses to the existing camera-phone such that the collection NA on the object side is larger would increase the magnification of the system (which, as discussed above, must currently work at a demagnification of ~0.01). Such an increase in $NA_{obj}$ would also increase both the light-gathering capacity of the system and the resolution it could achieve in terms of imaging a sample. The cost of this would be a reduction in field-of-view, which is not a major issue for the applications considered.

E. Microscopy Techniques: All techniques discussed here, including Dark Field, Differential Interference Contrast, Phase Contrast, Epi-illumination, etc., are well known to those with ordinary skill in the art and can be found in many standard references.

F. 1:1 Imaging: The phone was clearly not designed for 1:1 imaging. However, this could be a useful system for the purposes of microscopy, disease diagnosis, and the like, since it would yield resolution of approximately the size of the pixels in the detector array in the phone. Furthermore, lenses for the phone may be cheaply available due to the large quantities the phones manufactured, and could potentially be coupled to existing phones cheaply such that the imaging system was 1:1. Such a use is clearly novel for a cell-phone camera.

G. Small Aperture: Including an aperture in the optical system (potentially smaller than the existing apertures in the phone) such that the aperture stop for the entire system is defined by that aperture, would allow for construction of a doubly-telecentric system even if the current phone is not even telecentric in image space. This would allow for full control over the light collection and imaging efficiency of the phone, in particular allowing it to be made uniform across the entire field of view. Furthermore it would allow resolution to be uniform across the same field of view.

Examples of Uses of the Invention

Disease diagnosis in areas where more sophisticated microscopes are unavailable. Diagnosis possibly via computer image processing of an image taken with the cell-phone microscope and sent to a remote computer, possibly via cell-phone (wireless) communication. Image evaluation may also be by a human looking at the image from a remote location after it has been sent to him or her for such purpose.

Any other use where a low-cost, convenient, compact, or robust optical imaging and recording system with magnification higher than typical for a cell-phone camera is required.

Accordingly, the invention includes the following aspects among others:

1. An optical system consisting of a cell phone with built-in camera and at least one additional lens affixed to and oriented with respect to the cell phone camera such that the optical system has a collection numerical aperture (NA) of at least 0.001:

(a) The system of aspect 1 where the collection NA≥0.01

(b) The system of aspect 1 where the collection NA≥0.1

(c) The system of aspect 1 where the collection NA≥0.2

(d) The system of aspect 1 where the collection NA≥0.3

(e) The system of aspect 1 where the collection NA≥0.9

(f) The system of aspect 1 such that it magnifies the object≥5×

(g) The system of aspect 1 such that it magnifies the object≥10×

(h) The system of aspect 1 such that it magnifies the object≥15×

(i) The system of aspect 1 such that it magnifies the object≥20×

(j) The system of aspect 1 such that it magnifies the object≥25×

(k) The system of aspect 1 such that it magnifies the object≥50×

(l) The system of aspect 1 such that it has variable magnification

2. An optical system utilizing a cell-phone camera as the detection element wherein the optical system is telecentric on the object side.

3. An optical system utilizing a cell-phone camera as the detection element wherein the optical system is telecentric on the image side.

4. An optical system utilizing a cell-phone camera as the detection element wherein the optical system is doubly telecentric (i.e., telecentric on both the object and image sides).

5. An optical system satisfying both aspect 1 and any of aspects 2-4.

6. An optical system using a cell-phone camera as the detection element where the system is used to collect fluorescence as part of a biological fluorescence assay.

7. An optical system using a cell-phone camera as the detection element where the imaging system makes use of dark-field illumination or any variation on a dark-field optical technique.

8. An optical system using a cell-phone camera as the detection element where the imaging system makes use of the phase-contrast technique.

9. An optical system using a cell-phone camera as the detection element where the imaging system makes use of modulation contrast techniques, e.g. Hoffman modulation contrast.

10. An optical system using a cell-phone camera as the detection element where the imaging system makes use of the differential interference contrast technique (DIC).

11. An optical system using transmitted light microscopy to image a sample.

12. An optical system using reflected light microscopy to image a sample.

13. An optical system using light emitting diodes (LEDs) as an illumination source.

14. An optical system using a monochromatic LED as an illumination source.

(a) The system of aspect 14 to minimize the effect of chromatic aberrations.

(b) The system of aspect 14 to act as a fluorescent excitation source.

15. An optical system with a light source of one of more LEDs (or other illuminating sources) arranged to illuminate a sample.

16. An optical system using reflected light microscopy whereby one or more illumination sources (e.g. LEDs) are angled at the sample plane.

17. An optical system using transmitted light microscopy whereby a grid of one or more illumination sources illuminates a sample.

18. An optical system using Kohler illumination to evenly illuminate a sample.

19. An optical system using a diffuser element to evenly illuminate a sample.

20. An optical system with an illumination source powered by the cell phone.

21. Any of aspects 6-19 in combination with aspect 1.

22. Any of aspects 6-19 in combination with any of aspects 2-4.

23. Any of aspects 6-19 in combination with any of aspects 2-4 and in combination with aspect 1.

24. An optical system including a cell-phone camera which is used for disease diagnosis.

25. An optical system including a cell-phone camera which is used for medical evaluation of a patient's symptoms.

26. An optical system including a cell-phone camera which is used for a biological assay. Such assays could include, but are not limited to hematological analysis, blood counts, immunoassays, examinations or recording of tissue sample morphologies or pathology.

27. Aspect 26 in combination with aspect 1.

28. Aspect 26 in combination with aspect 1 and/or any of aspects 2-4 and/or any of aspects 6-10 and/or any of aspects 24-25.

29. An optical system including a cell-phone which is used for diagnosis or evaluation of any of the following: malaria, yaws, rashes, wounds, etc.

30. A system wherein a cell-phone camera is used in conjunction with a microfluidic device for disease or pathogen diagnosis.

31. A system wherein a cell-phone camera is used as part of the detection arm of a fluorescence assay, wherein the function of the emission filter for said assay is provided by the Color Filter Array (CFA) of the cell-phone camera.

32. A system wherein a cell-phone camera is used as part of the detection arm of a fluorescence assay where the separate color channels of the cell-phone camera are used separately to conduct 2 or more parallel assays at different emission wavelengths.

33. The system of aspect 1, wherein the autofocus mechanism of a cell-phone camera is used as part of the focusing mechanism.

34. A biological assay where optical detection is provided by a cell-phone camera and the pixels are binned to reduce image noise.

35. An optical system including a cell-phone camera as part of the detection arm wherein the illumination is epi-illumination.

36. The optical system of aspect 1, wherein the system is used for materials analysis. For instance, such analysis could include (but is not limited to) inspection of a metal part for metal fatigue, or evaluation of a weld, or evaluation of a component (e.g. a contact) in a micro-circuit.

37. The use of an optical system including a cell-phone camera as part of health monitoring in food service environments, e.g. for inspection of surfaces for bacteria.

38. Any use of a cell-phone camera wherein the sample being imaged is stained with any of the standard biological tissue stains, e.g. Gram staining.

39. The use of a cell-phone camera to collect autofluorescence of biological samples under ultraviolet excitation. Such excitation can be of any wavelength between 200 and 400 nm, or a combination thereof.

40. The use an optical system utilizing a cell-phone camera as part of the detection arm for quantification or comparison of protein concentration in a solution(s).

(a) The system of aspect 40 wherein the wavelength used for protein concentration evaluation is converted to a visible wavelength (or to one which is transmitted by the cell-phone camera lens and color filters) by a phosphor element or screen.

41. Use of a multichannel-plate intensifier in a system including a cell-phone camera as a detection element.

(a) Aspect 41 in conjunction with aspect 1.

(b) Aspect 41 where the system is used for a biological assay or evaluation of a biological sample.

42. The use of a cell-phone camera as part of the detection arm of a system for performing a DNA-based assay.

43. The use of a cell-phone camera as part of the detection arm of a system for performing a bioassay wherein illumination is supplied by a laser diode.

44. The use of a cell-phone camera as part of the detection arm of a system for performing a bioassay wherein illumination is supplied by an ultraviolet LED.

45. The use of a cell-phone camera as part of the detection arm of a system for performing a bioassay wherein illumination is supplied by a LED.

(a) The system of aspect 45 where the LED produces a power of >1 mW.

(b) The system of aspect 45 where the LED produces a power of >5 mW.

46. An optical system utilizing a cell-phone camera as a detection element wherein the system incorporates an aperture stop which is not co-local with the cell-phone camera's built-in lens(es).

47. An optical system utilizing a cell-phone camera as a detection element wherein the system incorporates an aperture smaller than the clear aperture of the cell-phone camera's built-in lens(es).

48. Any of the above aspects wherein the imaging system consists of a cell-phone camera coupled to at least one other lens, where the additional lens(es) constitute, in conjunction with the cell-phone camera, a symmetrical 1:1 imaging system.

49. Any of the above aspects, wherein "detector array coupled to a cellular telephony device" is substituted for "cell-phone camera".

50. A system of any of the above aspects wherein the optical system includes an apodizing filter to compensate for " cos 4th"-type vignetting effects for off-axis image points.

51. A program running on a cell phone which sends a signal to an external device which is part of the overall optical system or its mechanical components based on analysis of an image taken by the cell-phone camera.

(a) The system of aspect 51 in conjunction with aspect 1.

(b) The system of aspect 51 in addition to any of the above aspects.

52. An optical system including a camera-phone which has a total system magnification of $M \geq 0.01$.

(a) The system of aspect 52 with $M \geq 0.1$.

(b) The system of aspect 52 with $M \geq 0.2$ (c) The system of aspect 52 with $M \geq 0.5$ (d) The system of aspect 52 with $M \geq 0.9$ (e) The system of aspect 52 with $M \geq 1.0$ 53. Any of the above aspects wherein the lens system affixed to (or arranged next to) the phone is a zoom lens system.

(a) The system of aspect 53 where the zoom lens system is adjustable.

54. Any of the above aspects wherein the lenses are immersion lenses, to achieve higher magnification 55. Any of the above aspects used for evaluation of humans, animals, or plants (for crop health and disease evaluation)

56. An entire optical system that is either detachable from the cell phone or permanently affixed.

The invention also includes the following additional features in combination with the optical systems having aspects 1 and/or 2-4, and/or 6-10 listed above.

1. The optical systems in conjunction with a sample holder or stage allowing for manual motion to fixed positions (e.g. by use of mechanical indents) or indexed movement to simplify the acquisition of multiple fields of view.

2. The optical systems in conjunction with a sample holder or stage allowing for automated motion (e.g., but not limited to, using stepper motors) to allow for acquisition of multiple fields of view without direct user intervention.

(a) The system wherein the number of different fields of view captured is varied automatically by software depending on data acquired during the serial acquisitions, e.g., but not limited to, a system in which bacilli are automatically counted using image processing techniques, and images of different fields of view are acquired until the total bacillus count exceeds a given threshold or a threshold for total number of acquisitions is reached.

3. The optical systems in conjunction with GPS or location sensing via cellular methods (e.g. but not limited to cellular tower triangulation).

4. The optical systems in conjunction with automated appending of location data to image data, using location sensing capability such as GPS or cellular triangulation.

5. The optical systems in conjunction with a built-in ultraviolet light-emitting diode (UV LED) positioned such that the UV light serves to sterilize the sample area or other areas of the device which might become contaminated.

(a) The system where the UV LED illumination is confined by design to the interior of the device or such that it is only present (LED is only on) when a cover is properly closed, such that the user cannot come in contact with damaging UV radiation.

6. The optical systems in conjunction with a built-in fluorescence signal standard which allows for calibration of signal measured from samples, e.g., but not limited to, a "standard slide" with known standard fluorescent beads which is permanently positioned such that the sample-holder positioning motors can position said standard slide for image acquisition and then shift position to the sample slide. Other methods could include optics to direct a known intensity of light in a known pattern at the sample position, which light can be acquired by the collection optics and the resultant image used for calibration purposes.

7. The optical systems in conjunction with a filter or filters in the illumination path to select or limit the excitation wavelengths from LED, incandescent, or other excitation sources.

(a) The system where a set (of more than one) filters can be changed manually.

(b) The system where (of more than one) filters can be changed manually from a set of pre-installed filters on a variable positioning device (e.g. a filter slider or wheel).

(c) The system where the filter (or one of the filters) is acousto-optical (e.g. an acousto-optic tunable filter)

(d) The system where one or more filters is an interference filter.

(i) The system where the interference filter transmission spectrum is modified by turning the filter along an axis normal to the optic axis such that the incident angle of the light on the filter varies and hence causes the transmission of the filter to shift.

(e) The system where the one or more of the filters affects polarization instead of or in addition to wavelength.

(f) The system where the filter or one of the filters is an LCD spatial light modulator affecting polarization or transmission or both in an addressable manner for multiple pixels.

8. The optical systems in conjunction with filters in the collection path to select or limit the wavelengths passing to the focal plane sensor array (e.g., but not limited, to, a CCD or CMOS camera).

(a) The system where a set (of more than one) filters can be changed manually.

(b) The system where (of more than one) filters can be changed manually from a set of pre-installed filters on a variable positioning device (e.g. a filter slider or wheel).

(c) The system where the filter (or one of the filters) is acousto-optical (e.g. an acousto-optic tunable filter)

(d) The system where one or more filters is an interference filter.

(i) The system where the interference filter transmission spectrum is modified by turning the filter along an axis normal to the optic axis such that the incident angle of the light on the filter varies and hence causes the transmission of the filter to shift.

(e) The system where the one or more of the filters affects polarization instead of or in addition to wavelength.

(f) The system where the filter or one of the filters is an LCD spatial light modulator affecting polarization or transmission or both in an addressable manner for multiple pixels.

9. Either of systems 7 or 8 where the filter position is in an area of converging or diverging light, and the filter is an absorption filter (e.g., but not limited to, Schott glass GG495) such that the filter transmission is not a strong function of incident angle.

(a) The system where the half-angle of the cone of converging or diverging light is $\geq 0.5°$.

(b) The system where the half-angle of the cone of converging or diverging light is $\geq 2°$.

(c) The system where the half-angle of the cone of converging or diverging light is $\geq 4°$.

(d) The system where the half-angle of the cone of converging or diverging light is $\geq 10°$.

(e) The system where the half-angle of the cone of converging or diverging light is $\geq 20°$.

(f) The system where the half-angle of the cone of converging or diverging light is $\geq 30°$.

(g) The system where the half-angle of the cone of converging or diverging light is $\geq 40°$.

10. The optical systems in conjunction with an autofocus mechanism based on image processing, in conjunction with objective or sample movement by, e.g., but not limited to, a stepper motor or piezoelectric actuator. This system could work, e.g. (but not limited to) maximizing sharpness of edges (and/or content of high spatial frequencies) in a sample image to determine best focus, repositioning, retesting this criterion, and in an iterative manner converging on the position of best focus.

11. The optical systems where the illumination and/or collection optics are specifically designed to accommodate standard plastic or glass capillaries or cuvettes used for sample preparation and loading, e.g., but not limited to, having the optical system designed for proper spherical aberration correction when imaging through the wall of a cuvette.

12. The optical systems where the system is designed such that a capillary mounts directly in front of the collection optics 13. The optical systems where the system is designed such that a capillary or microfluidic device mounts directly on the sensor.

14. The optical systems where the software for the system allows for user-determined identification of region of interest of an image for transmission, e.g., but not limited to, allowing the user to define using a mouse, touch-screen, or pointer a specific region of an image to append to the sample data before saving or transmission.

(a) The system where such limitation reduces required transmission bandwidth or time (e.g., but not limited to, also reducing cost of data transmission).

15. The optical systems where the software for the system software automatically identifies a region of interest of an image for transmission, e.g., but not limited to, an area containing particles located via image processing, to append to the sample data before saving or transmission.

(a) The system where such limitation reduces required transmission bandwidth or time (e.g., but not limited to, also reducing cost of data transmission).

16. The optical systems where software operating in the device performs automated cell or particle counting using a defined algorithm.

17. The optical systems where the user is provided location-specific prompts, e.g. (but not limited to) prompts to select the patient record from a database of local patients, and/or prompted to visit or collect data from patients in the local area who are due for another test.

18. The optical systems where the database used is suitable for or compatible with standard or mobile web browsers.

The invention may further include the following systems and features, in combination with any and all of the above described systems and features.

1. A device for fluorescence microscopy where the optical image magnification (M) between the sample and the detector array is chosen such that the image of a typical sample (e.g., but not limited to, a fluorescently stained tuberculosis bacillus) spans a minimum number of pixels that is greater than the diffraction or aberration-limited spot size a point source in the sample would create at the detector array.

(a) For example, for a 0.4 NA, M=10, diffraction-limited imaging system, imaging a monochromatic source emitting light of a wavelength ($\lambda$) of $\lambda$=550 nm, the point-spread-function (PSF) would span a nominal distance (defined as the distance between zeros of the Airy disk) of $\delta=1.22\lambda*M/NA=16.8$ µm. For a system with 7.4 µm on-a-side square pixels, this spot would cover a minimum of 9 pixels.

2. A fluorescence microscope wherein the sample excitation is direct ("transillumination") and the "emitter filter" is placed at normal incidence directly in the back focal plane (BFP) (or as close as practical to the BFP) of the objective such that it reflects a substantial portion of the excitation (roughly that portion of the excitation collected by the objective, taking into account transmission losses in the objective, etc) directly back through the objective to the sample, thus increasing excitation intensity at the sample, though at the cost of increased background (and commensurate reduction in signal to noise (S/N) ratio) due to "crosstalk" (aka leakage) of the excitation wavelengths through to the detector.

(a) For example, for 0.67 NA condenser optics and a 0.4 NA objective, total excitation at the sample would be increased by $\sim \sin^2(a \sin(0.4)/2)/\sin^2(\sin(0.67)/2)=32\%$. ($\sin^2(a \sin(NA)/2)$=collection efficiency of a lens)

(b) Normally excitation is done using a dichroic and reflecting the excitation through the objective, such that little excitation actually ever impinges on the emission filter, which thus must block a smaller fraction of the total excitation power. Direct illumination is unusual.

3. A fluorescence system using direct excitation as above, where an absorbing filter (e.g. Schott glass GG495, 3 mm thick) is placed between an interference filter and the camera in order to further block excitation leakage to the detector.

(a) This is not standard practice for fluorescence microscopes, which universally use interference filters.

4. A fluorescence system where the window between the collection objective and the sample is made of a material that absorbs the excitation wavelengths.

(a) A system where a lens in the collection system absorbs said excitation wavelengths.

5. A fluorescence system wherein the emission filter is mounted near either the sample or image plane, to save cost since a smaller filter may be used in such a location.

6. A system wherein the particle counting algorithm includes both lower bounds and upper bounds.

7. A system wherein the upper and lower particle counting bounds are varied as a function of position on the detector array based on pre-determined variation in the PSF and/or RMS spot size for the optical system as a function of position on the detector array.

(a) This takes into account the possibility that aberrations/PSF are not uniform across the field of view, but vary (probably, but not necessarily, grow worse) towards the edge of the field.

8. A system wherein the particle counting algorithm incorporates an explicit threshold based in part on the signal-to-noise ratio (SNR) of the pixels at the location of the image of the (possible) particle.

9. A system wherein the particle counting algorithm involves calculating the "optical mass" (defined as the sum of pixel intensities above the background and, possibly, a noise threshold (e.g., but not limited to, three (3) standard deviations of background noise above the background mean, as determined on either a full-array basis, a column basis, a row basis, or a pixel-by-pixel basis) for all pixels potentially to be counted as part of the particle image) of the potential particle.

(a) A system wherein the thresholding criteria for counting a particle or including a given pixel as part of the particle image depends on the ratio of the optical mass to the background noise of the relevant pixels.

(b) A system wherein the thresholding criteria for counting a particle or including a given pixel as part of the particle image depends on the ratio of the optical mass to the distribution of the optical masses of all particles tentatively counted by the algorithm, the count of the putative particle being rejected if its optical mass falls more than a predetermined distance from that of the other potential particle counts (e.g., but not limited to, the particle optical mass falling greater than 2 (two) standard deviations above the mean of all potential particle optical masses.

10. A system where the particle counting algorithm includes a criterion for non-circularity of the particle image, e.g., but not limited to, a criterion that the particle have an ellipticity ratio of major to minor axes of other than 1:1.

(a) Same system, with ellipticity ratio of 4:3 or 3:2

(b) Same system, with ellipticity ratio determined by: (number of pixels in Airy disk diameter):(same number+1).

(i) Same system with ellipticity ratio determined by (number of pixels in Airy disk diameter) divided by (same number+2), (same number+3), etc.

11. A system wherein the particle counting algorithm incorporates

SNR-based thresholding, pixel size upper and lower bound, optical mass, and non-circularity criteria (a) A system where the counting algorithm involves any combination of the above criteria.

12. Detector array used for fluorescence imaging where the on-chip output amplifier of a non-cooled detector array is turned off during image acquisition to reduce "amplifier glow".

13. System where the excitation light is modulated to zero (or low) power except during that portion of the detector clock cycle where the image is being collected (a) LEDs not steadily on, or even on during the entire imaging time, but only during the actual CCD integration time—if the CCD has 1 msec shutter times at 30 fps (33 ms per image), that would amount to a 33× reduction in required power to the LEDs.

14. System where widefield fluorescence excitation is provided by a laser, and speckle in the illumination pattern is averaged out during the course of the detector integration time by modulation of the spatial mode structure of the laser output.

(a) System where the laser spatial mode modulation is accomplished via current modulation of a laser diode (b) System where the laser spatial mode modulation is accomplished via piezo (or other mechanical) modulation of the laser cavity; in the case of a laser diode, of the diode itself 15. System where a slide with a sample smear on the surface (e.g., but not limited to, blood or sputum, with no coverslip) is inserted into a holder and action of the device subsequently:

(a) Heats the slide to aid in or speed drying and heat-fixing of the sample.

(b) A device which seals a coverslip to a slide.

(c) A system where user safety is enhanced by automated staining (where technician doesn't come into contact with staining agents.

(i) Possibly in conjunction with blowing air over the sample.

(ii) Heating by blowing of hot air on the sample.

(1) Where the air is filtered to remove particulates before being blown on the sample.

(iii) Heating by conduction (e.g. resistive heater coupled to the slide by action of the device or the nature of the holder—e.g. a copper holder which is heated & serves to heat the slide).

(1) Where the heat is preferentially applied near the center of the slide where the sample smear would normally be located, rather than at the edges or uniformly over the entire slide.

(d) Seals a chamber over the slide (e.g. by forcing a chamber with O-ring seal against the area of the slide normally covered by the smear), OR around the slide.

(i) Slides with an area marked to delimit the area over which to smear sample.

(e) Chamber is flushed with a staining solution (as, for example, the BD Auramine O staining kit solutions).

(i) Followed by a rinse.

(ii) Followed by a destaining solution.

(iii) Followed by a rinse.

(iv) Followed by heating and/or blowing air to dry the slide.

(v) Repeat to cover the entire slide preparation process.

(f) Said solutions, including rinse water, or contained in the device or mounted to it.

(g) Waste solution is collected in or on the device for later disposal.

(h) Slide is subsequently imaged.

(i) Without user touching it (e.g. chamber is removed, and slide either is already in position or is then automatically positioned for imaging).

(j) Wherein the staining procedures are for Auramine staining of TB, general staining of acid-fast-bacilli (AFB), or malaria.

(j) Where the fluorescent stain is not antibody-linked.

(k) Where fluors are antibody-linked.

16. System where multiple fields-of-view (FoVs) are imaged by automatic repositioning of the slide (a) System where user repositions slide using a manipulator (such that slide and optics remain enclosed, separated from room light), then pushes a single button to acquire the image.

17. System where imaging element (e.g. detector array, possibly including some or all optical elements) can be removed from the system for use in another, different system while remaining connected (or connectable) to the image processing and/or transmission device(s), e.g., but not limited to, a webcam which is removable along with a single attached lens, which assembly has an external size allowing it to be slipped into a standard microscope eyepiece tube and where the attached lens allows the microscope intermediate image normally acquired by the user's eye to be imaged on the detector array.

(a) Where the different system is a standard microscope with eyepiece tube.

(b) Where the removable element has standard dimensions to fit in, on, or over a standard microscope eyepiece tube.

(c) Where the "some" optical elements permanently attached to the imaging array will serve to produce appropriate focus of an intermediate image from the microscope onto the detector array.

(d) Where the removable element has standard dimensions to fit in, on, or over a standard microscope eyepiece.

(e) Where the "some" optical elements permanently attached to the imaging array will serve to produce appropriate focus of an intermediate image from the microscope onto the detector array.

(f) Where the fluorescence emission filter is included in the removable component including the detector array.

(g) Where the emission filter is NOT included in the removable component.

18. Power supply robust to voltage spikes and low/over voltage conditions.

(a) System where insensitivity to voltage spikes is achieved through a choke on the power input line.

(b) System where such a choke is followed by a DC-DC converter.

19. System where particles are counted, and data is uploaded via a telephone link.

(a) Where data includes a processed image.

(b) Where data does not include any image, only count and patient identifier.

(c) Where additional patient data is included.

(d) Where a small field of the total processed image is included for reference, but not the entire image (e.g., but not limited to, for purposes of saving bandwidth).

(e) Where data is stored on the device for later upload.

(f) Where data is transferred by wireless or wired connection to a nearby computer.

20. Encryption for patient data.

(a) Encryption to a public key for the organization.

21. System where LEDs are off unless system is presenting an image for focusing or acquiring an image(s) for analysis.

22. Software which prompts the user for the required number of image fields.

(a) Same for slides.

(b) Where a warning is flashed if count in one field is high, and in a second very low (or vice-versa) (e.g. to catch if a field is contaminated, or a field was taken off the smear area).

(i) And the image (or a portion thereof) is presented to the user to verify acceptability.

(c) Where user is prompted to OK an image field before it is logged to the record (e.g., but not limited to, checking that image is in focus/whatever).

23. Where prior patient data is downloaded over the communications link after the initial record information is entered prior to a new test.

(a) Where this data is compared to subsequent test results, giving the test administer immediate feedback as to whether the patient has improved or not, or may require immediate care.

(b) Where said prior data is downloaded to the system before the user takes it out into the field.

24. System where the image pixels are binned prior to display on a screen of smaller pixel size than that of the total imaging array, where the binning is designed to increase image SNR.

(a) System where the image displayed for focusing purposes is also digitally enhanced (e.g., but not limited to gain and/or scaling applied in software or firmware) to aid visibility to the user of faint particles in the sample.

25. System where materials of different thermal coefficients of expansion are used in the optical mounting system to make it insensitive to temperature changes, allowing a longer period between refocusings.

From the foregoing, it can be seen that the present invention involves adding high numerical aperture optics to the existing optics and image sensor of a camera in a cellphone or other telecommunications device to form an optical system capable of recording and transmitting high resolution microscopy images. Design of the system could include different modes of microscopy, including bright field, dark field, phase, differential interference contrast (DIC), polarization, and fluorescence.

For fluorescent imaging, the built-in Bayer color filter on the camera sensor could serve as filters for fluorescence at three different wavelengths. Additionally, software could be written that would allow the phone to refocus for each of the wavelengths captured by the image sensor. This could reduce chromatic aberrations for any color image, fluorescent or otherwise. The 8 bits of each of the three color channels could also be used for high dynamic range post-processing of images, which could provide additional sensitivity for certain applications, such as disease diagnosis.

Finally, for continual or periodic monitoring uses, image acquisition could be triggered by a key event, such as water level changes, motion sensors, pH level changes, or simply time lapsed.

The invention has wide applicability, including but not limited to the following:

1. Disease diagnosis from blood samples including but not limited to parasitic or bacterial infections (e.g. malaria, Chagas, Leishmaniasis, sleeping sickness, sepsis, gonorrhea, *N meningititis* infection), disorders of the red blood cells (sickle cell anemia, thalassemia, anemia, lead poisoning, spherocytosis, pyruvate kinase disease), disorders of the white blood cells (leukemia, Chedik-Higashi syndrome, vitamin deficiencies), and platelet disorders (low count, immune mediated thrombocytopenic purpura).

2. Disease diagnosis from urine samples (urinary tract infection, kidney stones).

3. Disease diagnosis from spinal fluid (meningitis).

4. Disease diagnosis from synovial fluid (gout).

5. Disease diagnosis from sputum (tuberculosis, pneumonia, cystic fibrosis).

6. Disease diagnosis from lesions or pus (yaws, lyme disease).

7. Disease diagnosis from tissue samples (cancer).

8. Disease diagnosis or screening requiring fluorescent images (HIV, anything with known antibody staining techniques, cancer).

For each of the foregoing applications, existing sample preparation methods including staining and fixation could be used to provide proper contrast and repeatable imaging results. The device could also be coupled to existing diagnosis devices, such as microchip-based devices.

Additional applications include, but are not limited to:

1. Microscopy of soil or water samples in the field.

2. Remote and/or continuous monitoring of soil or water samples.

3. Monitoring or testing of materials for fatigue or failure.

4. Monitoring or testing of circuitry.

5. Immediate microscopy of microorganisms that cannot be cultured in a lab setting.

6. Monitoring of materials, soil, water samples.

7. Any of the above uses with advanced microscopy techniques, e.g. phase contrast, differential interference contrast, polarization, darkfield, etc.

8. Any of the above uses with automated image processing.

9. Any of the above uses with automated triggering of image acquisition.

It will be appreciated, therefore, that current technology presents an "either/or" problem with telemicroscopy: either the technology includes advanced microscopy suitable for specialized applications but requires a computer for data storage and internet connection for data transmission, or the "microscopy" device coupled to a camera phone is insufficient for any advanced microscopy, which would be essential for usefulness in the applications above.

The present invention bridges the gap in existing technologies by coupling high numerical aperture optics to a camera phone (or other suitable telecommunications device) for the ability to immediately capture and transmit high resolution images with a single device. This technology, unlike conventional advanced microscopy, would be highly portable and, considering the prevalence of telecommunications networks worldwide, would be usable in remote locations. And unlike a low numerical aperture device, this technology would be useful in a wide variety of microscopy applications. Finally, the light-capturing ability of high numerical aperture optics would allow this technology to be used for fluorescent images, where signal-to-noise ratios can be quite low.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art. In the appended claims, reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present disclosure. Moreover, it is not necessary for a device or method to address each and every problem sought to be solved by the present invention, for it to be encompassed by the present disclosure. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A telemicroscopy imaging system for making a wireless communications device into a microscope, the system comprising:
    a portable, hand-held microscope housing;
    an image sensor mounted in the microscope housing;
    collection optics mounted in the microscope housing and aligned with the image sensor, the collection optics having a collection numerical aperture (NA) of at least approximately 0.01 and a magnification (M) of at least about 1;
    an illumination source mounted in the housing and positioned to illuminate a sample;
    a wireless transmission unit mounted in the housing for transmitting data from the image sensor to the wireless communications device, wherein the wireless communications device has a microprocessor for controlling data collection, analysis and transmission.

2. The imaging system of claim 1, wherein the microprocessor is programmed to derive medically relevant information from an acquired image.

3. The imaging system of claim 2, wherein the microprocessor is programmed to implement a particle counting algorithm.

4. The imaging system of claim 1, wherein the microprocessor is programmed to extract medically relevant information from an acquired image via automatic image processing.

5. The imaging system of claim 1, further comprising a GPS or other location sensing unit, wherein the microprocessor is programmed to add location data to image data transmitted by the wireless transmission unit.

6. The imaging system of claim 1, wherein the microprocessor is programmed to allow user-determined identification of a region of interest of an image for transmission.

* * * * *